(12) United States Patent
Segman

(10) Patent No.: US 9,844,345 B2
(45) Date of Patent: Dec. 19, 2017

(54) COMBINATION NON-INVASIVE AND INVASIVE BIOPARAMETER MEASURING DEVICE

(71) Applicant: CNOGA MEDICAL LTD., Or Akiva (IL)

(72) Inventor: Yosef Segman, Or Akiva (IL)

(73) Assignee: CNOGA MEDICAL LTD., Or Akiva (IL)

( * ) Notice: Subject to any disclaimer, the term of this patent is extended or adjusted under 35 U.S.C. 154(b) by 436 days.

(21) Appl. No.: 14/582,221

(22) Filed: Dec. 24, 2014

(65) Prior Publication Data

US 2015/0141778 A1    May 21, 2015

Related U.S. Application Data

(63) Continuation of application No. 13/011,903, filed on Jan. 23, 2011, now Pat. No. 8,948,833.

(51) Int. Cl.

| | |
|---|---|
| *A61B 5/1455* | (2006.01) |
| *A61B 5/145* | (2006.01) |
| *A61B 5/1495* | (2006.01) |
| *A61B 5/00* | (2006.01) |
| *A61B 5/01* | (2006.01) |
| *A61B 5/053* | (2006.01) |
| *A61B 5/1459* | (2006.01) |
| *A61B 10/00* | (2006.01) |

(52) U.S. Cl.
CPC .......... *A61B 5/7246* (2013.01); *A61B 5/0022* (2013.01); *A61B 5/01* (2013.01); *A61B 5/053* (2013.01); *A61B 5/1455* (2013.01); *A61B 5/1459* (2013.01); *A61B 5/1495* (2013.01); *A61B 5/14532* (2013.01); *A61B 5/486* (2013.01); *A61B 5/7225* (2013.01); *A61B 5/7267* (2013.01); *A61B 5/7278* (2013.01); *A61B 5/742* (2013.01); *A61B 10/00* (2013.01); *A61B 2010/0083* (2013.01)

(58) Field of Classification Search
CPC . A61B 5/1459; A61B 5/14532; A61B 5/1455; A61B 5/14558; G06T 7/0012
See application file for complete search history.

(56) References Cited

U.S. PATENT DOCUMENTS 7,620,674 B2 * 11/2009 Ruchti ............... A61B 5/14532
708/400

* cited by examiner

*Primary Examiner* — Eric Winakur
(74) *Attorney, Agent, or Firm* — Mark M. Friedman

(57) ABSTRACT

In a combination invasive and non-invasive bioparameter monitoring device an invasive component measures the bioparameter and transmits the reading to the non-invasive component. The non-invasive component generates a bioparametric reading upon insertion by the patient of a body part. A digital processor processes a series over time of digital color images of the body part and represents the digital images as a signal over time that is converted to a learning vector using mathematical functions. A learning matrix is created. A coefficient of learning vector is deduced. From a new vector from non-invasive measurements, a new matrix of same size and structure is created. Using the coefficient of learning vector, a recognition matrix may be tested to measure the bioparameter non-invasively. The learning matrix may be expanded and kept regular. After a device is calibrated to the individual patient, universal calibration can be generated from sending data over the Internet.

30 Claims, 9 Drawing Sheets

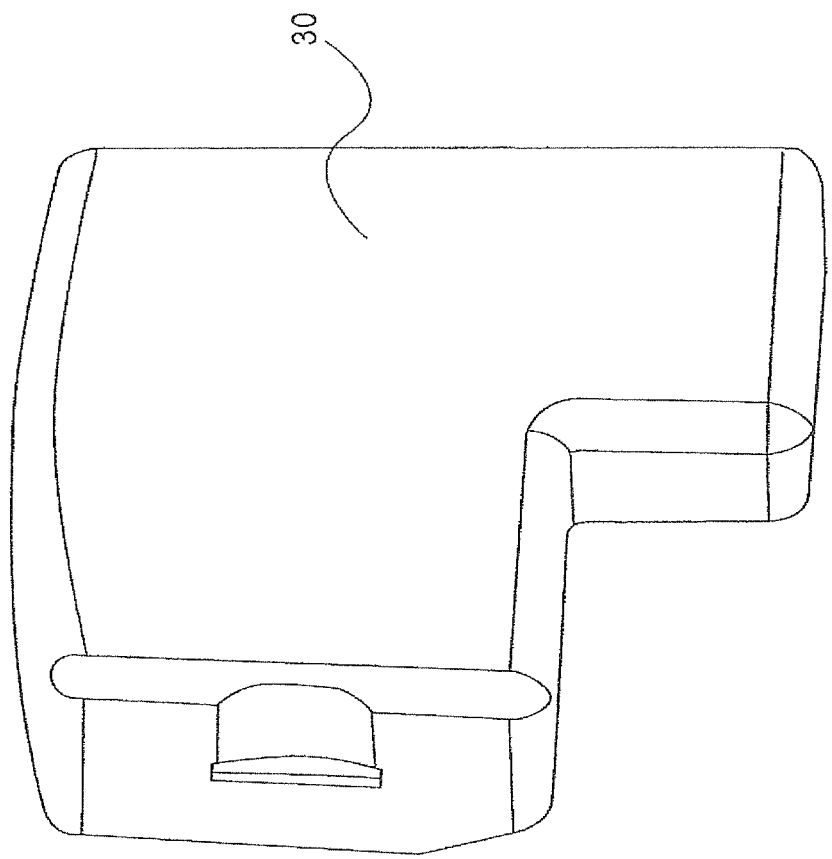

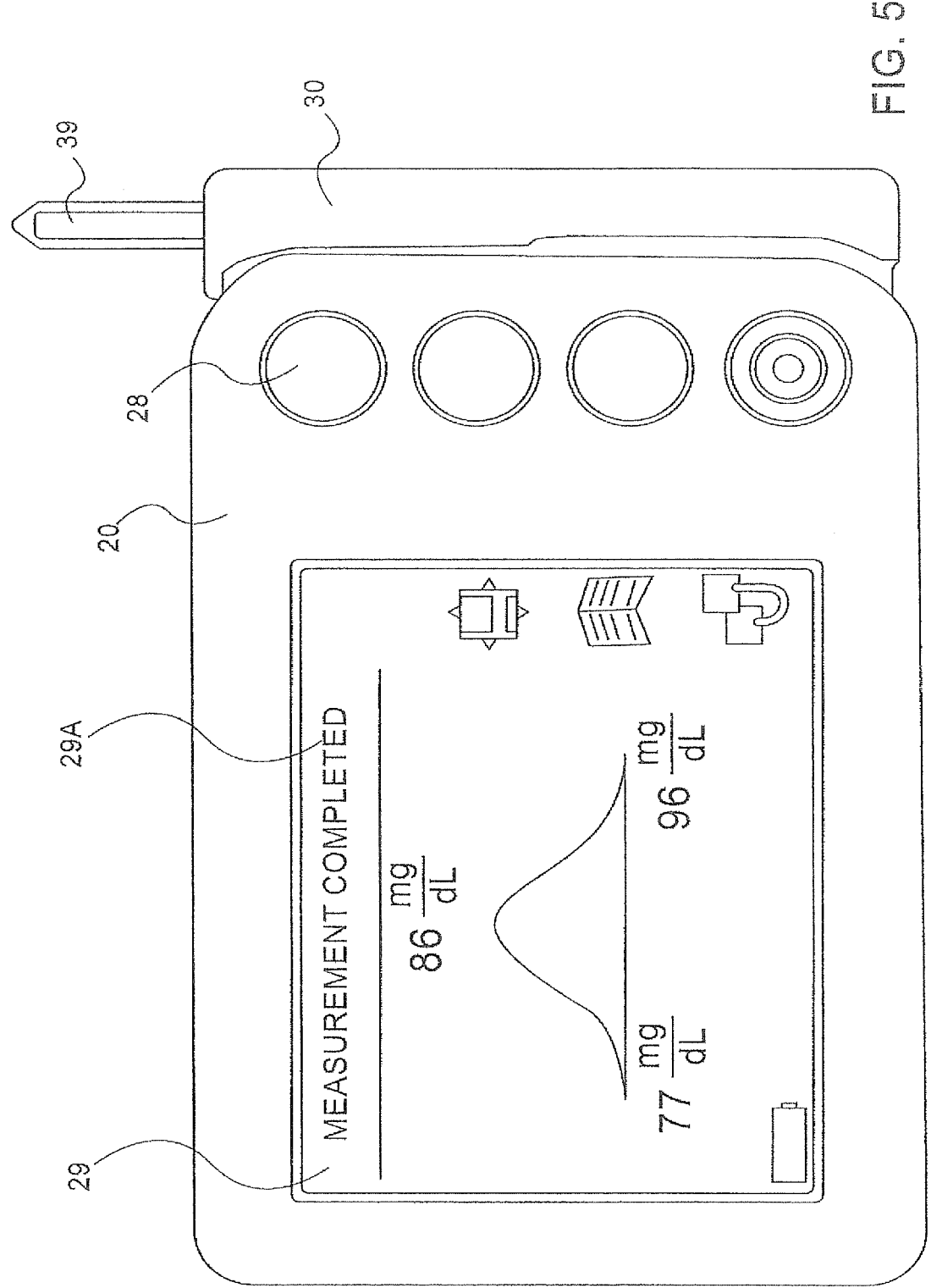

METHOD - 100

INVASIVELY MEASURING THE BIOPARAMETER OF A PATIENT USING AN INVASIVE COMPONENT OF A BIOPARAMETER MONITORING DEVICE AND TRANSMITTING AN INVASIVE BIOPARAMETER READING TO A NON-INVASIVE COMPONENT OF THE BIOPARAMETER MONITORING DEVICE THE INVASIVE BIOPARAMETER READING TO BE ENTERED IN A COLUMN VECTOR, Y ⟶ 110

WITHIN A PROXIMITY TIME OF STEP "110", NON-INVASIVELY MEASURING THE BIOPARAMETER OF THE PATIENT BY USING ONE OR MORE COLOR IMAGE SENSORS IN THE NON-INVASIVE COMPONENT OF THE DEVICE TO GENERATE A SERIES OF COLOR IMAGES OF TISSUE OF A BODY PART OF THE PATIENT AND TO SENSE A MAGNITUDE OF EACH OF THREE COLORS AT PIXELS OF EACH COLOR IMAGE AND BY CONVERTING THE MAGNITUDES INTO A SERIES OF ELECTRIC SIGNALS, TO PRODUCE A SIGNAL OVER TIME REFLECTING A DISTRIBUTION OF EACH OF THE THREE COLORS IN THE COLOR IMAGES OVER TIME ⟶ 120

A DIGITAL PROCESSOR OF THE NON-INVASIVE COMPONENT (I) USING A MATHEMATICAL FUNCTION TO CONVERT THE SIGNAL TO A SCALAR LEARNING NUMBER AND (II) REPEATING STEP "130(I)", WITHOUT NECESSARILY USING THE SAME MATHEMATICAL FUNCTION, TO FORM A LEARNING VECTOR THAT CORRESPONDS TO A SCALAR INVASIVE BIOPARAMETER READING ENTRY OF COLUMN VECTOR Y ⟶ 130

FROM A PLURALITY OF LEARNING VECTORS, A DIGITAL PROCESSOR FORMING AN N BY N LEARNING MATRIX, D, THAT IS A REGULAR MATRIX, BY REPEATING STEPS "110" THROUGH "130" ENOUGH TIMES THAT A DIGITAL PROCESSOR HAS SUFFICIENT CORRELATIONS BETWEEN NON-INVASIVE BIOPARAMETRIC READINGS AND INVASIVE BIOPARAMETRIC READINGS TO BE ABLE TO MEASURE THE BIOPARAMETER USING A NON-INVASIVE BIOPARAMETER READING AT A PRE-DEFINED LEVEL OF THRESHOLD ACCEPTABILITY ⟶ 140

FIG. 6A

| METHOD – 100 - CONTINUED |

| A DIGITAL PROCESSOR OBTAINING A COEFFICIENT OF LEARNING VECTOR, C, BY MULTIPLYING AN INVERSE MATRIX $D^{-1}$ OF LEARNING MATRIX, D BY THE COLUMN VECTOR Y |

— 150

| A DIGITAL PROCESSOR OBTAINING A NEW VECTOR, $V^{NEW}$ BY (I) NON-INVASIVELY MEASURING THE BIOPARAMETER OF THE PATIENT BY USING THE ONE OR MORE COLOR IMAGE SENSORS IN THE NON-INVASIVE COMPONENT OF THE DEVICE TO GENERATE A SERIES OF COLOR IMAGES OF TISSUE OF A BODY PART OF THE PATIENT AND TO SENSE A MAGNITUDE OF EACH OF THE THREE COLORS AT PIXELS OF EACH COLOR IMAGE AND BY CONVERTING THE MAGNITUDES INTO A SERIES OF ELECTRIC SIGNALS, TO PRODUCE A SIGNAL OVER TIME REFLECTING A DISTRIBUTION OF EACH OF THE THREE COLORS IN THE COLOR IMAGES OVER TIME AND BY HAVING A DIGITAL PROCESSOR USE A MATHEMATICAL FUNCTION TO CONVERT THE SIGNAL TO A SCALAR NUMBER AND BY (II) REPEATING STEP "160(I) N TIMES TO FORM $V^{NEW}$, WITHOUT NECESSARILY USING THE SAME |

— 160

| USING THE ENTRIES OF $V^{NEW}$ TO FORM A REGULAR MATRIX, $D^{NEW}$, OF N BY N SIZE AND WHOSE STRUCTURE OF NON-ZERO ELEMENTS IS IDENTICAL TO A STRUCTURE OF NON-ZERO ELEMENTS OF LEARNING MATRIX, D |

— 170

| USING A DIGITAL PROCESSOR TO PERFORM A MATRIX VECTOR MULTIPLICATION OF $D^{NEW}$ BY COEFFICIENT OF LEARNING VECTOR, C, TO CREATE A COLUMN VECTOR OF NON-INVASIVE BIOPARAMETER MEASUREMENT, R, AND COMPARING ENTRIES OF R WITH ENTRIES OF Y TO FIND ONE ENTRY OF R WHICH REPRESENTS A CALIBRATED BIOPARAMETER VALUE FOR THE PATIENT |

METHOD – 200

↓

PROVIDING TO A PATIENT A MEDICAL DEVICE HAVING (I) A NON-INVASIVE COMPONENT CAPABLE OF GENERATING A NON-INVASIVE BIOPARAMETRIC READING OF THE PATIENT'S BIOPARAMETER UPON INSERTION BY THE PATIENT OF A BODY PART INTO THE NON-INVASIVE COMPONENT, THE NON-INVASIVE COMPONENT INCLUDING A FIRST DIGITAL PROCESSOR FOR PROCESSING DIGITAL COLOR IMAGES OF PART OF THE BODY PART AND REPRESENTING THE DIGITAL IMAGES AS A DISCRETE SIGNAL OVER TIME, AND HAVING (II) AN INVASIVE COMPONENT FOR MEASURING THE BIOPARAMETER FROM BLOOD OF THE PATIENT AND OBTAINING AN INVASIVE BIOPARAMETRIC READING FOR THE PATIENT, THE INVASIVE COMPONENT ALSO INCLUDING A SECOND DIGITAL PROCESSOR FOR TRANSMITTING THE INVASIVE BIOPARAMETRIC READING TO THE FIRST DIGITAL PROCESSOR OF THE NON-INVASIVE COMPONENT

↳ 210

↓

CALIBRATING THE NON-INVASIVE COMPONENT TO THE PATIENT BY (I) INVASIVELY MEASURING THE BIOPARAMETER OF THE PATIENT, (II) TRANSMITTING THE INVASIVE BIOPARAMETER READINGS TO THE NON-INVASIVE COMPONENT, AND (III) NON-INVASIVELY MEASURING THE BIOPARAMETER OF THE PATIENT WITHIN A PROXIMITY TIME OF THE INVASIVE MEASURING USING MATHEMATICAL FUNCTIONS, AND PERFORMING SUBSTEPS (I), (II) AND (III) ENOUGH TIMES THAT THE DIGITAL PROCESSOR HAS SUFFICIENT CORRELATIONS BETWEEN NON-INVASIVE BIOPARAMETRIC READINGS AND INVASIVE BIOPARAMETRIC READINGS TO BE ABLE TO MEASURE THE BIOPARAMETER USING A NON-INVASIVE BIOPARAMETER READING AT A PRE-DEFINED LEVEL OF THRESHOLD ACCEPTABILITY

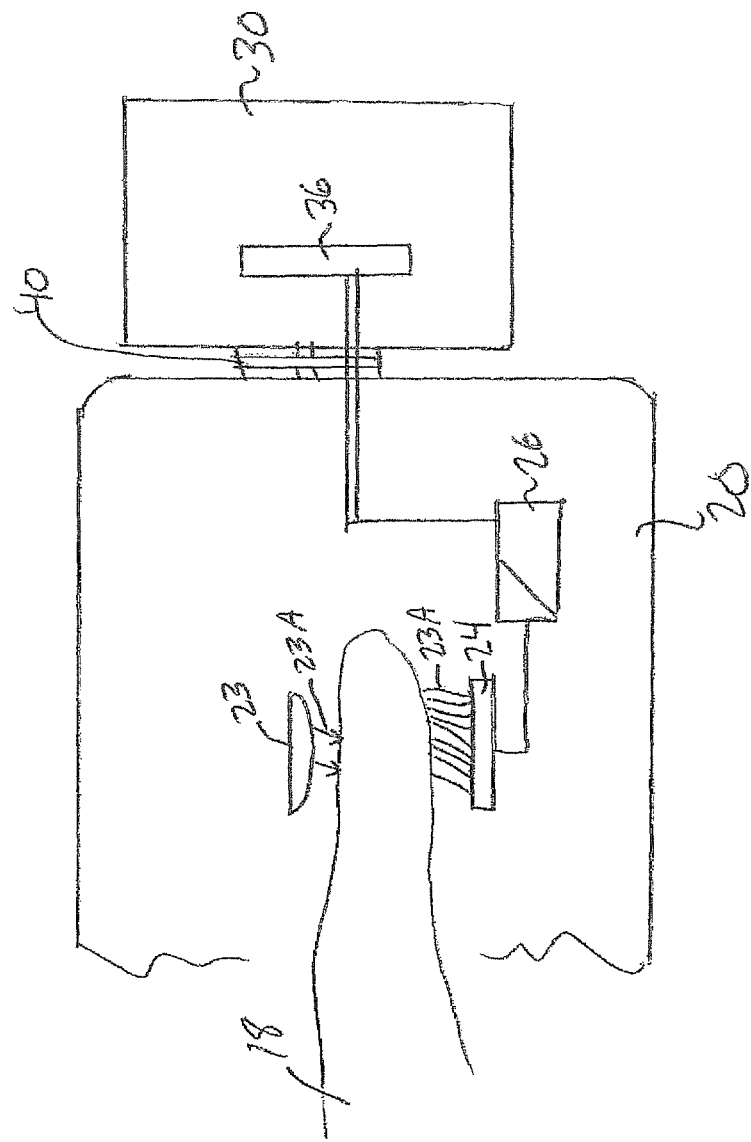

COMBINATION NON-INVASIVE AND INVASIVE BIOPARAMETER MEASURING DEVICE

FIELD AND BACKGROUND OF THE INVENTION

The present invention relates to apparatuses and methods for non-invasive bioparameter monitoring and, more particularly to a combination non-invasive and invasive bioparameter measuring device and method.

A 2006 summary of the failed non-invasive glucose monitoring techniques entitled "The Pursuit of Noninvasive Glucose: Hunting the Deceitful Turkey" ("The Pursuit of Noninvasive Glucose" or "PNG") written by John Smith, former chief scientific officer at Lifescan, a Johnson & Johnson subsidiary, details why over the last 25 years there has not been a successful non-invasive glucose monitoring device. This background discussion is based primarily on this book.

Diabetes is a serious disease that can cause eye damage, kidney damage, loss of feeling in the extremities, slow healing of wounds, amputation of toes, feet or legs and cardiovascular disease. See PNG at page 7. If patients adhere strictly to a proper diet, exercise, take medication and make frequent measurements of blood glucose they are able to maintain their health and lead relatively normal lives. Id. It is therefore critical to monitor blood glucose. To accurately measure blood glucose levels, one needs to measure the amount of glucose in the blood itself (as opposed to the urine) and this is done by dedicated devices for measuring blood glucose level invasively at home or in doctors' offices and laboratories millions of times every day. See Id. Such devices require painful intrusion, which is uncomfortable and carries a risk of contamination for the individual. Sticking oneself with a sharp object to draw blood is unpleasant and even traumatic, especially since it must be done repeatedly daily over many years.

In addition, in order for people with diabetes to maintain healthy levels of glucose there has always been a need for simple, accurate tests that patients can perform at home. See id. If simple, non-invasive, inexpensive, reliable tests were available, they could measure their glucose non-invasively often at home. See id.

According to "The Pursuit of Noninvasive Glucose", each year, hundreds of thousands of people are newly diagnosed with diabetes, because rising standards of living in the developed world encourage a diet prone to high glucose. The immense market size (as of 2007 over $7 billion worldwide) and the demand has led to constant announcements by fledgling companies that the problem of a non-invasive blood glucose monitoring system has been solved. In fact, no successful device has yet been developed to allow patients to measure their glucose non-invasively without pain or trauma. According to "The Pursuit of Noninvasive Glucose" oxygen saturation is measured by the ratio of the amount of hemoglobin that has oxygen attached to the amount that does not have oxygen attached. Oxy hemoglobin is bluish while deoxyhemoglobin is a visibly different color, namely bright red. Significantly, hemoglobin is the only compound in the body with a strong blue or red color and it exists almost exclusively inside red blood cells, which travel inside blood vessels in well-defined paths. It is therefore relatively easy to use spectroscopic techniques to measure oxygen saturation in the body non-invasively.

In contrast to hemoglobin, glucose has nondescript characteristics—it is colorless, it varies in concentration from one part of the body to another and it exists in much smaller concentrations than hemoglobin. See PNG at pages 26-28. Furthermore, the chemical structure of glucose as a hydrocarbon with multiple hydroxyl groups also makes it very similar to many other compounds in the body and in fact glucose is attached to most of the proteins in the body. Spectroscopic techniques for detecting glucose have had difficulty distinguishing signals of protein molecules that are attached to glucose and which may correlate with glucose from signals of glucose molecules alone. For example, the near infrared region has many weak, overlapping, varying spectroscopic signals that come from hydrocarbons with multiple hydroxyl groups.

Moreover, the spectroscopic signals reflected from tight striking glucose molecules are weak. Accordingly, when attempting to find correlations between a data set and a true glucose measurement, it is very hard to successfully use mathematical algorithms to separate variations within the data set into a series of curve shape components to account for decreasing amounts of observed variability.

In addition, spectroscopic techniques often show initially promising correlations between variations of a spectroscopic effect with true glucose concentrations but when later checked against variations in room temperature and humidity, it turns out that these local environmental variations account for the correlation. See The Pursuit of Noninvasive Glucose at p. 66. As a result, no reliable and accurate technique ends up getting developed.

A further problem is that to determine how well a parameter is a good measure of glucose concentration, the procedure is to have the patient drink 50 to 100 grains of glucose in a single drink will not be effective because "almost every measured physiological parameter (i.e. core temperature, surface temperature, peripheral perfusion, skin hydration, electrolyte balance, gastric motility, peripheral edema, enzyme levels, galvanic skin response, respiration, urine production, saliva production) shows strong correlation with the curve in an oral glucose tolerance test". See The Pursuit of Noninvasive Glucose at page 60.

"Noninvasive glucose measurements have been attempted by an incredibly diverse range of technologies." The Pursuit of Noninvasive Glucose at p. 28. None of them have succeeded during the last 25 to 30 years. Although correlations between certain qualities and glucose have been alleged to have been found using spectroscopic analysis, no non-invasive product using such techniques have to date ever been successful or even workable in terms of accurately and reliably measuring glucose. See The Pursuit of Noninvasive Glucose. This may be because the alleged correlations were never real to begin with since they were not verified in light of environmental or other parameters. No method of calibrating data from a non-invasive measurement to predict the actual glucose level in the body based on invasive measurements as the reference point has succeeded to a reliable and accurate point.

Besides glucose, there are many other bioparameters that it would be useful to be able to monitor accurately and reliably, particularly by a portable device usable by a consumer or a patient at home. Such bioparameters can for example include oxygen and carbon dioxide concentration, urea nitrogen, systolic and diastolic blood pressure, moisture, dryness, saltiness, pH, tissue saturation (for example external skin tissue, internal muscle), tissue vitality (for example internal tumor tissue or external skin melanoma represents different skin vitality) red blood cell count (number or concentration of cells per one cubic millimeter), stroke volume variation (amount of blood injecting out from the heart in every stroke) and skin vessel deformation, cholesterol, potassium, systolic and diastolic blood pressure, stroke volume, chloride, sodium, nitrogen, hemoglobin, bilirubin, cholesterol LDL, HDL and total cholesterol, percentage of $CO_2$, percentage of $O_2$, red blood cells, white blood cells, iron, hematocrit, platelets, etc.

There is therefore a compelling need for an accurate and reliable apparatus and method for a non-invasive bioparameter measuring device, particularly where glucose is the bioparameter, although not limited to such a case. There is a further need for such an apparatus and method which is portable enough and easy enough to use that it may be usable by patients at home.

SUMMARY OF THE PRESENT INVENTION

One aspect of the present invention is directed to a method of monitoring a bioparameter, comprising (a) invasively measuring the bioparameter of a patient using an invasive component of a bioparameter monitoring device and transmitting an invasive bioparameter reading to a non-invasive component of the bioparameter monitoring device, the invasive bioparameter reading to be entered in a column vector, Y; (b) within a proximity time of step "(a)", non-invasively measuring the bioparameter of the patient by using one or more color image sensors in the non-invasive component of the device to generate a series of color images of tissue of a body part of the patient and to sense a magnitude of each of three colors at pixels of each color image and by converting the magnitudes into a series of electric signals, to produce a signal over time reflecting a distribution of each of the three colors in the color images over time; (c) a digital processor of the non-invasive component (i) using a mathematical function to convert the signal to a scalar learning number and (ii) repeating step "(c)(i)", without necessarily using the same mathematical function, to form a learning vector that corresponds to a scalar invasive bioparameter reading entry of column vector Y; (d) from a plurality of learning vectors, forming an n by n learning matrix, D, that is a regular matrix, by repeating steps "(a)" through "(c)" enough times that a digital processor has sufficient correlations between non-invasive bioparametric readings and invasive bioparametric readings to be able to measure the bioparameter using a non-invasive bioparameter reading at a pre-defined level of threshold acceptability; (e) obtaining a coefficient of learning vector, C, by multiplying an inverse matrix $D^{-1}$ of learning matrix, D by the column vector Y; (f) obtaining a new vector, $V^{new}$ by (i) non-invasively measuring the bioparameter of the patient by using the one or more color image sensors in the non-invasive component of the device to generate a series of color images of tissue of a body part of the patient and to sense a magnitude of each of the three colors at pixels of each color image and by converting the magnitudes into a series of electric signals, to produce a signal over time reflecting a distribution of each of the three colors in the color images over time and by having a digital processor use a mathematical function to convert the signal to a scalar number and by (ii) repeating step "(f)(i) a times to form $V^{new}$, without necessarily using the same mathematical functions; (g) using the entries of $V^{new}$ to form a regular matrix, $D^{new}$, of n by n size and whose structure of non-zero elements is identical to a structure of non-zero elements of learning matrix, D; and (h) using a digital processor to perform a matrix vector multiplication of $D^{new}$ by coefficient of learning vector, C, to create a column vector of non-invasive bioparameter measurement, R, and comparing entries of R with entries of Y to find one entry of R which represents a calibrated bioparameter value for the patient.

A further aspect of the present invention is directed to a portable bioparameter-monitoring medical device usable by a patient, comprising a non-invasive component capable of generating non-invasive bioparametric readings of tissue of a body part of the patient upon insertion by the patient of a body part of the patient into the non-invasive component, the non-invasive component including at least one color image sensor to generate a series of color images of the tissue and to sense a magnitude of each of three colors at pixels of each color image, and including a first digital processor for processing the series of color images into a signal over time reflecting a distribution of each of the three colors over time; an invasive component for obtaining an invasive bioparametric reading from blood of the patient, the invasive component also including a second digital processor for automatically transmitting the invasive bioparametric reading to the first digital processor of the non-invasive component, the invasive bioparametric readings forming entries in a column vector, Y, the non-invasive component programmed to (a) (i) use a mathematical function to convert the signal to a scalar learning number and (ii) repeat step "(a)(i)", without necessarily using the same mathematical functions, to form a learning vector that corresponds to a scalar invasive bioparameter reading entry of column vector Y; (b) form an n by n learning matrix, D, that is a regular matrix, by repeating step "(a)" to non-invasive readings and invasive readings enough times that the first digital processor has sufficient correlations between non-invasive bioparametric readings and invasive bioparametric readings to be able to measure the bioparameter based on a non-invasive bioparameter reading of the bioparameter at a pre-defined level of threshold acceptability; (c) to obtain a coefficient of learning vector, C, by multiplying an inverse matrix $D^{-1}$ of matrix, D by the column vector, Y; (d) generate a new vector, $V^{new}$ when a user non-invasively measures the bioparameter of the patient by using the one or more color image sensors in the non-invasive component of the device to generate a series of color images of tissue of the body part and by having the digital processor use a mathematical function to convert the signal to a scalar number and doing so n times to form $V^{new}$, without necessarily using the same mathematical functions; (e) use the entries of $V^{new}$ to form a regular matrix, $D^{new}$, of n by n size and whose structure of non-zero elements is identical to learning matrix, D, and (f) use a digital processor to perform a matrix vector multiplication of $D^{new}$ by coefficient of learning vector, C, to create a vector of non-invasive bioparameter measurement, R, and comparing entries of R with entries of Y to find one entry of R which represents a calibrated bioparameter value for the patient.

A still further aspect of the present invention involves a method of producing a portable bioparameter-monitoring medical device custom-tailored to a patient, the method comprising (a) providing directly or indirectly to a patient a medical device having (i) a non-invasive component capable of generating a non-invasive bioparametric reading of the patient's bioparameter upon insertion by the patient of a body part into the non-invasive component, the non-invasive component including a first digital processor for processing digital color images of part of the body part and representing the digital images as a discrete signal over time, and having (ii) an invasive component for measuring the bioparameter from blood of the patient and obtaining an invasive bioparametric reading for the patient, the invasive component also including a second digital processor for transmitting the invasive bioparametric reading to the first digital processor of the non-invasive component, and (iii) a coupling element for maintaining the invasive component operatively engaged to the non-invasive component and allowing transmission of invasive bioparametric readings from the invasive component to the non-invasive component, the first digital processor also for calibrating the non-invasive component so that the non-invasive bioparametric readings for the patient approximate the invasive bioparametric readings for the patient for a given bioparameter under a predefined standard of approximation; and (b) calibrating the non-invasive component to the patient by (i) invasively measuring the bioparameter of the patient using the invasive component, (ii) transmitting the invasive bioparameter readings to the non-invasive component, and (iii) non-invasively measuring the bioparameter of the patient within a proximity time of the invasive measuring using mathematical functions, and performing substeps (i), (ii) and (iii) enough times that the first digital processor has sufficient correlations between non-invasive bioparametric readings and invasive bioparametric readings to be able to measure the bioparameter using a non-invasive bioparameter reading at a pre-defined level of threshold acceptability.

A still further aspect of the present invention may be directed to a method of monitoring a bioparameter, comprising (a) invasively measuring the bioparameter of a patient using an invasive component of a bioparameter monitoring device and transmitting an invasive bioparameter reading to a non-invasive component of the bioparameter monitoring device, the invasive bioparameter reading to be entered in a column vector, Y; (b) within a proximity time of step "(a)", non-invasively measuring the bioparameter of the patient by using one or more variable sensors in the non-invasive component of the device to generate a series of data representing a magnitude of one or more variables of tissue of a body part of the patient and by converting the magnitudes into a series of electric signals, to produce a signal over time reflecting a distribution of each of the one or more variables over time; (c) digital processor of the non-invasive component (i) using a mathematical function to convert the signal to a scalar learning number and (ii) repeating step "(c)(i)", without necessarily using the same mathematical function, to form a learning vector that corresponds to a scalar invasive bioparameter reading entry of column vector Y; (d) from a plurality of learning vectors, a digital processor forming an n by n learning matrix, D, that is a regular matrix, by repeating steps "(a)" through "(c)" enough times that a digital processor has sufficient correlations between non-invasive bioparametric readings and invasive bioparametric readings to be able to measure the bioparameter using a non-invasive bioparameter reading at a pre-defined level of threshold acceptability; (e) a digital processor obtaining a coefficient of learning vector, C, by multiplying an inverse matrix $D^{-1}$ of learning matrix, D by the column vector Y; (f) a digital processor obtaining a new vector, $V^{new}$ by (i) non-invasively measuring the bioparameter of the patient by using the one or more variable sensors in the non-invasive component of the device to generate a series of data representing a magnitude of one or more variables of tissue of a body part of the patient and by converting the magnitudes into a series of electric signals, to produce a signal over time reflecting a distribution of each of the variables over time and by having a digital processor use a mathematical function to convert the signal to a scalar number and by (ii) repeating step "(f)(i) n times to form $V^{new}$, without necessarily using the same mathematical functions; (g) using the entries of $V^{new}$ to form a regular matrix, $D^{new}$, of n by n size and whose structure of non-zero elements is identical to a structure of non-zero elements of learning matrix, D; and (h) using a digital processor to perform a matrix vector multiplication of $D^{new}$ by coefficient of learning vector, C, to create a column vector of non-invasive bioparameter measurement, R, and comparing entries of R with entries of Y to find one entry of R which represents a calibrated bioparameter value for the patient.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 4 is a perspective view of the invasive component of the combination device of FIG. 1, in accordance with one embodiment of the present invention;

FIG. 5 is a front view of the device of FIG. 1, in accordance with one embodiment of the present invention;

FIGS. 6A-6B show a flow chart showing a method in accordance with one embodiment of the present invention;

FIG. 7 is a flow chart showing a further method in accordance with one embodiment of the present invention; and FIG. 8 is a schematic of the device of FIG. 1, in accordance with one embodiment of the present invention.

DETAILED DESCRIPTION OF THE INVENTION

Figure 1:
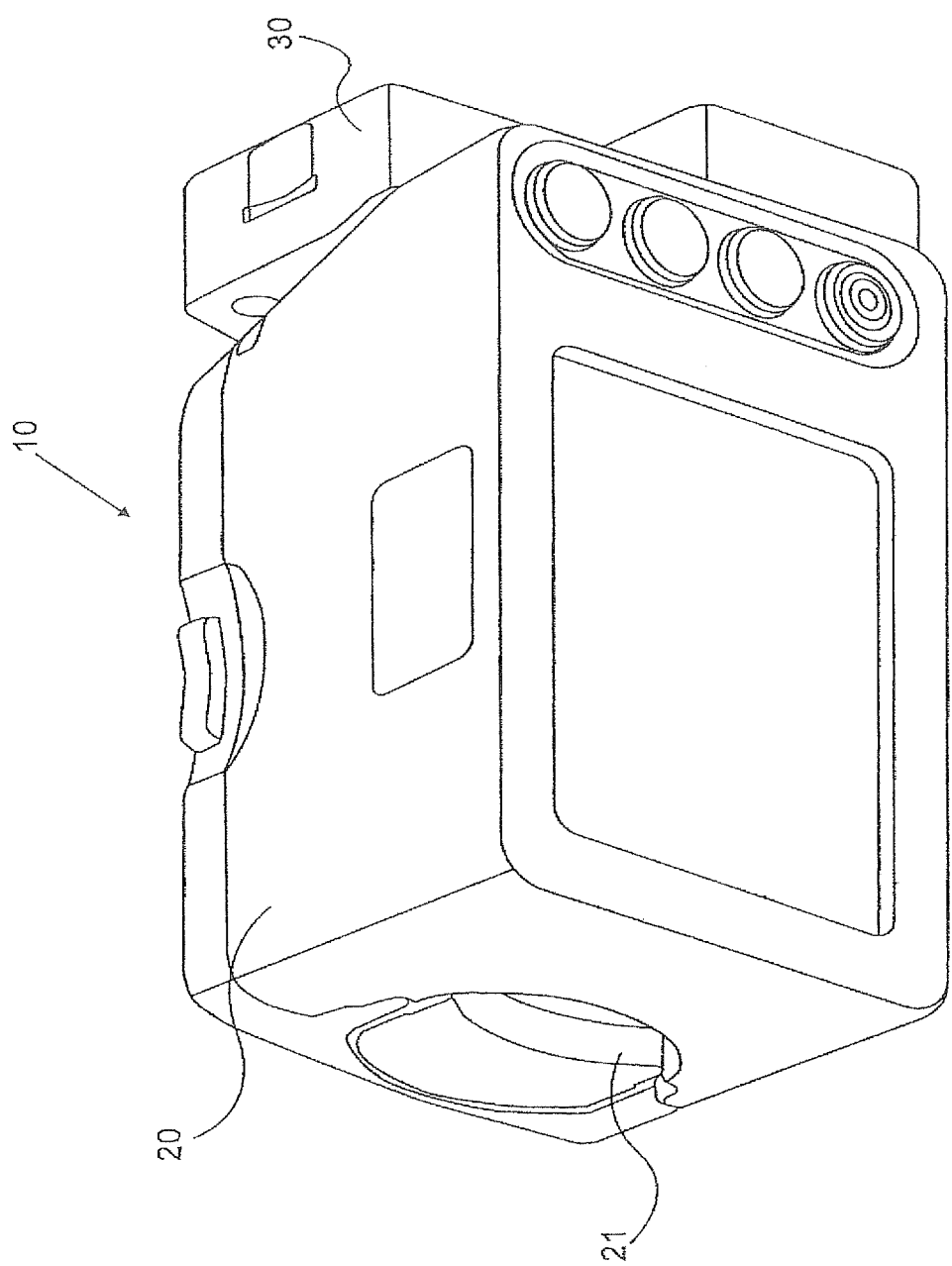
FIG. 1 is a left, front and side perspective view of a combination invasive and non-invasive bioparameter-monitoring device, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a combination non-invasive and invasive bioparameter monitoring device and method that may for example be used as a reliable and accurate non-invasive glucose monitoring device. The device may include a non-invasive component and an invasive component as well as a coupling device connecting these two components. The non-invasive component may be de-coupled from the invasive component or from the coupling element so as to allow the at least one of the non-invasive component and the invasive component to operate as a standalone device. In one version, a user may stick his finger to obtain blood and then measure the glucose or other bioparameter in the blood using the invasive component. Within a defined proximity time thereafter, the user may insert his finger into the non-invasive component where color image sensors may generate a signal over time based on a distribution of the magnitude of red, green and blue pixels in a series of color images over time. A digital processor of the non-invasive component may use mathematical functions to convert the signal to a scalar number. The may be repeated to create additional scalar numbers as entries to a learning matrix having a certain size and whose non-zero elements have a certain structure. Further non-invasive readings may be used to create a new vector and a new regular matrix of the same size and structure as the learning matrix may be created from the new vector. Then, using a coefficient of learning vector, a recognition matrix may be tested to measure the bioparameter non-invasively. The learning matrix may be expanded and kept as a regular matrix to make an accurate and reliable calibrated value for the bioparameter of the patient. Each medical device may therefore be custom-tailored to the user who purchases and uses the device. In a case where the bioparameter is glucose, each user may use A1C readings as invasive readings and may further verify the calibration and recalibrate the device if needed. By taking and entering data from a population, a universal or a cluster calibration may be achieved.

In contrast to prior art non-invasive methods for indirectly measuring a bioparameter, the method and device of the present invention may utilize an n by n regular learning matrix by taking a vector representing non-invasive bioparameter readings and using its entries to form a regular $D^{new}$ matrix of n by n size and whose structure of non-zero elements is identical to a structure of non-zero elements of the learning matrix, D and by using the digital processor to use a previously obtained coefficient of learning vector, C, to create candidate bioparameter values that may represent a calibrated bioparameter value for the patient. In further contrast to the prior, the learning matrix of the method of the present invention may be expanded by incorporating new non-invasive bioparametric measurements into learning matrix D so as to maintain expanded learning matrix $D_{exp}$ as a regular matrix and then test its accuracy by comparison to invasive readings. In further contrast to the non-invasive methods and apparatuses of the prior art for indirectly measuring or monitoring a bioparameter of a patient or subject, the method and apparatus of the present invention for non-invasive monitoring/measuring may be accurate and reliable for glucose and other bioparameters that are difficult to directly measure. In further contrast to the prior art measurement apparatuses that are non-invasive or invasive, the method and apparatus of the prior art may combine non-invasive and invasive components. In contrast to prior art non-invasive bioparameter devices, the device of the present invention may be calibrated by each patient to be custom-tailored to the individual. In still further contrast to the prior art, the method and apparatus of the present invention may calibrate a threshold non-invasive value of a bioparameter for a patient to approximate an invasive value by using mathematical functions to convert numbers representative of a signal generated from a change in color distribution over time based on separate matrices for blue, red and green (or other color bases such as yellow, cyan and magenta and use a coefficient of learning vector and further non-invasive measurements of the bioparameter to arrive at a reliable value for the bioparameter. In still further contrast to the prior art, the data from the patient's bioparameter value may be collected to form a cluster calibration and a universal calibration.

The principles and operation of an apparatus and method for a combination non-invasive and invasive bioparameter monitoring medical device according to the present invention may be better understood with reference to the drawings and the accompanying description.

The "bioparameters" that may be measured by the method or system of the present invention may include any bioparameter, for example glucose, oxygen and carbon dioxide concentration, urea nitrogen, systolic and diastolic blood pressure, moisture, dryness, saltiness, pH, tissue saturation (for example external skin tissue, internal muscle), tissue vitality (for example internal tumor tissue or external skin melanoma represents different skin vitality) red blood cell count (number or concentration of cells per one cubic millimeter), stroke volume variation (amount of blood injecting out from the heart in every stroke) and skin vessel deformation, cholesterol, potassium, systolic and diastolic blood pressure, stroke volume, chloride, sodium, nitrogen, hemoglobin, bilirubin, cholesterol LDL, HDL and total cholesterol, $pCO_2$, $pO_2$, red blood cells, white blood cells, iron, hematocrit, platelets, etc.

FIG. 1 shows a portable bioparameter-monitoring medical device 10 usable by a patient, comprising a non-invasive component 20, an invasive component 30 and a coupling element 40. Non-invasive component 20 may include a defined area 21 or recess into which patients may insert a finger or other body part. The term "patient" should be understood to be synonymous with "a subject" and is not intended to be limited to those suffering from illnesses. As shown in the schematic of FIG. 8, non-invasive component 20 may also include a light transmitting element 23, which as an example may be an LED or laser diode or other light source at various wavelengths (whether continuous or discrete) and may include a photodetector, such a photodiode that converts light to electric signals representing a color distribution of the tissue under consideration. As further seen in FIG. 8, a light transmitting element 23 may transmit light 23A through the finger 18 or other body part of the subject and generate digital color images from light exiting the body part. For example, a single color image sensor 24 for sensing red light, green light, and blue light may be used and adjusted (for example using filters) for the different lights or multiple color image sensors may be used, one for each of the three colors (red, blue, green).

The invention also contemplates that sensors may broadly encompass more than color image sensors and may even broadly encompass more than image sensors. In general, sensors 24 (sometimes called "variable sensors") may be used to sense a variable other than color. For example, sensors 24 or variable sensors 24 may be optical sensors, mechanical sensors, electrical sensors, chemical sensors or other sensors and may be used to sense other variables besides color such as temperature at a certain part of the tissue of the subject, electrical conductivity at a certain part of the tissue of the subject, smell, moisture, magnetic field or other variables associated with a part of the body of the subject and that may be correlate with a bioparameter of that subject. Accordingly, the following discussion that utilizes "color image" sensors should be understood to also contemplate utilizing other variable sensors. In that regard, the term "color image" obtained from a sensor may be replaced with "image" wherein "image" is taken broadly to mean any sensed variable whether visual or otherwise. Furthermore, the term "pixels" may be replaced with the term "portions" of the image. The sensed variable sensed by the variable sensor may in one embodiment be selected from the group consisting of temperature, conductivity and smell.

Non-invasive component 20 may be capable of generating a non-invasive bioparametric reading of the patient's bioparameter upon insertion by the patient of the finger or other body part into the non-invasive component. For example, the non-invasive component 20 may include a light transmitting element that transmits light through a finger or other body part and may generate digital color images from light exiting the finger or other body part.

Non-invasive component 20 may accomplish this by using a first digital processor 26 in conjunction with appropriate software for processing digital color images of part of the finger or other body part exposed et the light and representing the digital images as a discrete signal over time. For example, color image sensors 24 in the non-invasive component 20 of the device 10 may generate a series of color images of part of the finger of the patient and sense a magnitude of each of three colors at each pixel of each color image and convert the magnitudes into a series of electric signals, to produce a signal over time reflecting a distribution of each of the three colors in the color images over time. Accordingly, the discrete digital signal may incorporate a red matrix representing magnitudes of red light at pixels of a digital image of the finger, a green matrix representing magnitudes of green light at the pixels and a blue matrix representing magnitudes of blue light at the pixels.

Figure 2:
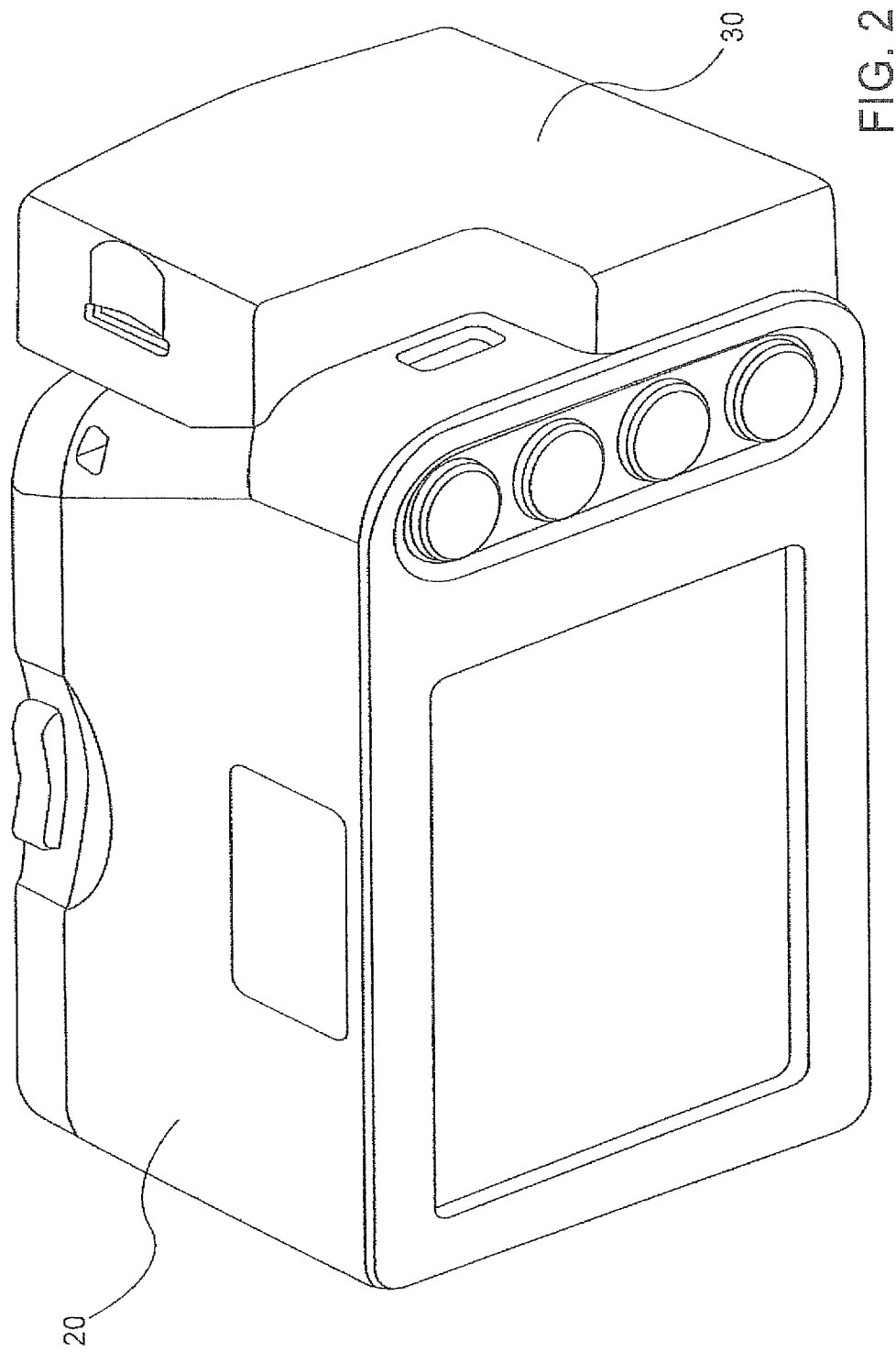
FIG. 2 is a right, front and side perspective view of the combination device of FIG. 1, in accordance with one embodiment of the present invention.
Figure 3:
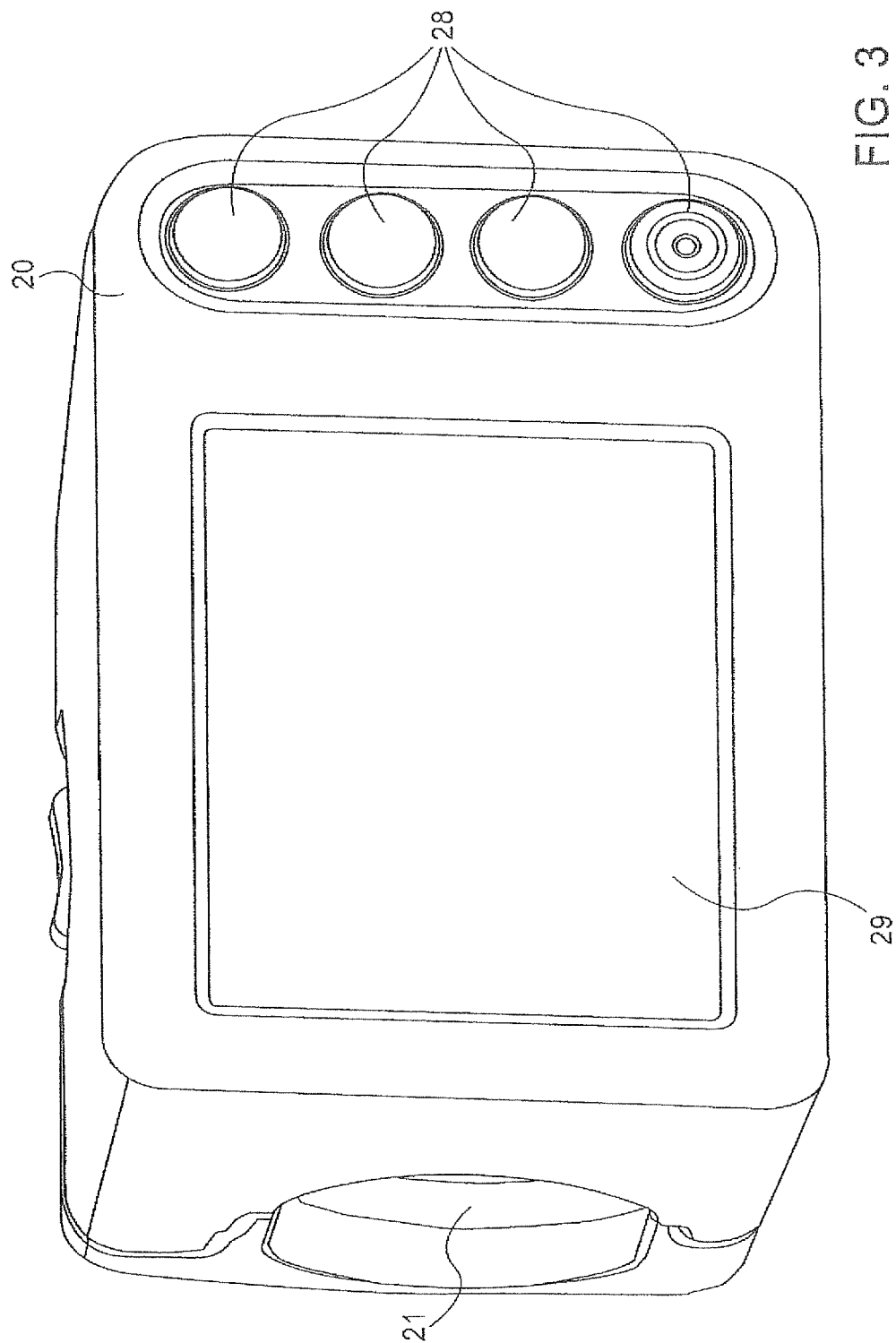
FIG. 3 is a front left perspective view of the non-invasive component of the combination device of FIG. 1, in accordance with one embodiment of the present invention.

As seen from FIG. 1 and FIG. 2, the combination medical device 10 may also include an invasive component 30. FIG. 4 illustrates one embodiment of an invasive component standing alone. Invasive component 30 may be used for invasively measuring the bioparameter, for example glucose, from blood of the patient (or in other cases from other fluid or tissue of the patient) and obtaining an invasive bioparametric reading for the patient. For example, the patient may stick himself and obtain blood and smear the blood onto a test strip 39 (see FIG. 5) for insertion into the invasive component 30, as is known in the art. The invasive component 30 may also include a second digital processor 36 that may be capable of storing the invasive reading of the bioparameter and may be capable of transmitting the invasive bioparametric reading to the non-invasive component, for example to the first digital processor 26 of non-invasive component 20.

Device 10 may also include a coupling element 40 for maintaining the invasive component 30 operatively engaged to the non-invasive component 20 and for allowing transmission of invasive bioparametric readings from invasive component 30 to non-invasive component 20. As shown in FIG. 8, coupling element 40 may be situated between invasive component 30 and non-invasive component 20 and may include a connector that connects non-invasive component 20 to invasive component 30. The connector may include a wire that connects USB ports between the noninvasive and invasive components 20, 30 or a wire that connects serial ports using an UART chip or wires using parallel ports. Alternatively, the connector may be a wireless receiver and transmitter useful in wireless communication. Accordingly, coupling element 40 may mechanically as well as electrically couple non-invasive and invasive components 20, 30 together. Notwithstanding FIG. 8, coupling element 40 may be integrated within non-invasive component 20 or within non-invasive component 30 as a port.

In some cases, device 10 may operate within a coupling mode wherein coupling element 40 may maintain invasive component 30 operatively engaged to non-invasive component 20 thereby allowing transmission of invasive bioparametric readings from invasive component 30 to non-invasive component 20. When coupling element 40 is in de-coupling mode, non-invasive component 20 and invasive component 30 may be de-coupled from one another.

In certain scenarios, non-invasive measurements or calibrated values for a bioparameter may be transmitted from non-invasive component 20 to invasive component 30. Once non-invasive component 20 has been calibrated and made reliable for measuring the bioparameter, it may be that the reliability of the non-invasive measurement by the non-invasive component may also be used to calibrate measurements taken invasively. Invasive component 30 may use the calibrated non-invasive measurement of the bioparameter to calibrate the invasive measurement of the bioparameter in this scenario.

It should be understood that first digital processor 26 and second digital processor 36 may be used in conjunction with software suitable for accomplishing the task of the processors. The software may be embedded upon a computer readable medium.

As shown in FIG. 6A and FIG. 6B, the present invention may be described as a method 100 of monitoring a bioparameter, in which the non-invasive component and the invasive component may be programmed to perform or help perform the steps of method 100. Method 100 may include a fast step 110 of invasively measuring the bioparameter of a patient using an invasive component of a bioparameter monitoring device (such as the invasive component 30 described in relation to device 10) and transmitting the resulting invasive bioparameter reading to the non-invasive component of the bioparameter monitoring device (such as the non-invasive component 20 of device 10). The invasive bioparameter reading may be entered as an entry in a developing column vector, Y and this may be performed by the non-invasive component 20 when the reading may be transmitted from the invasive component 30 to the non-invasive component 20 or in some scenarios it may be performed by the invasive component 30. For example, if the bioparameter is glucose, the patient may stick himself, places the blood on the test strip of the invasive component and then insert the test strip into the invasive component of the combination device 10. The device 10 may send the invasive bioparameter results to the non-invasive section of the device.

Method 100 may also involve a step 120 of, within a proximity time of step 110, non-invasively measuring the bioparameter of the patient by using one or more color image sensors in the non-invasive component of the device to generate a series of color images of tissue of a body part of the patient and to sense a magnitude of each of three colors at pixels of each color image and by converting the magnitudes into a series of electric signals, to produce a signal over time reflecting a distribution of each of the three colors in the color images over time. The proximity time may, depending on the bioparameter and known scientific information about the bioparameter, be a few seconds or 15 second or 30 seconds or a minute or a longer time, depending on the device but must be within a short enough time that the bioparameter has not significantly changed in that part of the patient.

For example, simultaneously or close in time to the taking of the invasive blood sample taking, the patient may insert his finger 18 (FIG. 8) into a designated area 21 of the non-invasive chamber 20 no that light may be sent through the tissue of the finger and exit the finger to strike an optical sensor. This may occur over a period of time, which may be, for example ten seconds. This finger may be the same finger as the finger from which an invasive measurement was taken or in some scenarios it may be a different finger or body part.

Purely as an example, 60 images per second may be taken of the finger part over 10 seconds. The series of 600 successive images produces data about each of three colors at each pixel of each image that may then be represented as a function S (X, t) which may equal $S(x_1, x_2, x_3, t)$. The function, S, may also include other variables such as $x_4$ which for example could be a measure of smell, electrical conductivity, temperature, and/or humidity in a particular location of the measurement of the patient's body part. In some version, the function, S, may not include color as one of the variables and may only include temperature, humidity, electrical conductivity, smell, etc measured by sensors other than image sensors. First digital processor 26 may calibrate the non-invasive component 20 so that the non-invasive bioparametric readings for the patient approximate the invasive bioparametric readings for the patient for a given bioparameter under a predefined standard of approximation, such as a predefined standard used in the industry.

In some versions, prior to step 110 the patient may connect the non-invasive component with the invasive component using a coupling element that may couple the invasive and non-invasive components. The proximity in time may be defined by scientific standards in the industry, and may be for example, 10, seconds, 15 seconds, 30 seconds, 45 seconds, 60 seconds, two minutes, three minutes, etc.

In a further step 130 of method 100, a digital processor of the non-invasive component (i) may use a mathematical function to convert the signal to a scalar learning number and (ii) may repeat step 130 part "(i)", without necessarily using the same mathematical function, to form a learning vector that may correspond to a scalar invasive bioparameter reading entry of column vector Y. The mathematical function for converting the signal into a scalar number representative of the signal may be any of a variety of such functions and this applies for all steps of method 100. One simple example would be a mathematical function that takes the average magnitude of all of the entries over time for all of the colors combined. Another example is a function that takes the average deviation of all of the entries over time for all of the colors combined. Other examples of such a function may be arrived at through partial differential solutions, wavelet transform, statistical computations, Fourier transform, spectral analysis, neural network computation, and linear and non linear equations. The size of the learning vector may depend on what structure of non-zero elements one chooses to have in learning matrix D formed from a plurality of learning vectors.

Accordingly, method 100 may have a further step 140 that may involve using a digital processor to form, from a plurality of learning vectors, an n by n learning matrix, D, that is a regular matrix, by repeating steps 110 through 130 enough times that the digital processor may have sufficient correlations between non-invasive bioparametric readings and invasive bioparametric readings to be able to measure the bioparameter using a non-invasive bioparameter reading at a pre-defined level of threshold acceptability. The pre-defined level of threshold acceptability may for example be a deviation of 5%, 10%, 20% etc., from a tested invasive measurement or any other appropriate industry acceptable mathematical or other standard. The repetitions may be continued until digital processor of the non-invasive component has made a sufficient correlation between non-invasive bioparametric readings and invasive bioparametric readings to be able to predict at a threshold level further invasive bio-parametric readings based on non-invasive bioparametric readings. The repetitions of taking the non-invasive measurements step 120 may involve the same body part of the same patient. For example, the patient may insert the same finger into the same non-invasive component. In other scenarios, the patient may insert other fingers or other body parts. In still other scenarios, the body parts of other patients may be used for non-invasive measurements, which as discussed more fully below, may yield a universal calibration.

The non-invasive measurements of the bioparameter of the patient may, for example, on each occasion be taken over say 10 seconds during insertion by the patient of a finger into defined area 21 of non-invasive component 20 on June 15. There may for example be 500 or 600 images taken over that second period by the optic sensors. The second row of the regular matrix, D, may represent non-invasive readings for the bioparameter over for example 10 seconds on June 16. The third row of the regular matrix, D, may represent non-invasive readings for the bioparameter over for example 10 seconds on June 17.

Accordingly, learning matrix D may have a specific structure of non-zero elements. One example may be to take each successive learning vector generated in proximity to an invasive bioparameter reading and make it a new row of learning vector D. While the invasive readings are gradually forming a column vector Y, the learning vectors are gradually forming a regular matrix, D. The structure of the nonzero entries of learning matrix, D, may be made triangular such that a magnitude of entries in each succeeding row increases by an integer. For example, the integer referred to may be "1".

For example, the first learning vector may be a single entry forming the first row of the learning matrix D. That is, on the first day or first occasion, only one mathematical function was applied to create one scalar number from the non-invasively obtained signal over time. Then, on the second day when a further non-invasive measurement was taken (again in proximity to an invasive reading), and a new signal created, two mathematical functions may be used to create two different scalar numbers from the signal and these two scalar numbers may form a second learning vector whose entries may be incorporated into the second row of the learning matrix D. On the third day or the third occasion in proximity to when a non-invasive reading is taken, a third learning vector may be created having three entries from three applications of different mathematical functions. This may go until one has an n by n regular matrix of a size that has a realistic chance of figuring out the bioparameter from a new electro-optical signal converted to a new vector. In the above example the structure of the non-zero entries of the matrix is triangular. For example, after ten occasions of non-invasive measurements on, say, ten days, the device may have has ten invasive readings and ten signals representing a function of the color matrices of the finger tissue.

After the tenth sample the display of the device may advise that no more invasive measurements are needed since enough has been learned from the correlations between the color matrices and the invasive bioparametric reading to have a realistic chance to predict to some threshold level of accuracy what the invasive result should be on the $11^{th}$ ((n+1)th) reading. As seen in FIG. 5, a display screen 29 on medical device 10, after step 140 of method 100, may also display a message (not shown) to a user of the medical device 10 to the effect that further invasive measurements are not needed. For example, the message may state that the device is calibrated, that the measurement is completed or that it is no longer necessary to stick oneself. Display screen 29 may also be used to display a graph of the signal, S developed by non-invasive component. Various buttons of other actuators 28 may be used to interact with device 10.

In contrast, the entries of vector Y may comprise one entry for each "row" in the column of vector Y, which may be n rows long. The matrix D may be placed alongside vector Y such that the n entries in, for example, the second row of matrix D may be correlated with the invasive reading entered in the second "row" of vector Y. Each entry of the learning matrix may represent certain computation of the tissue color distribution under consideration. In the case of measurements made continuously over time, the matrix D and the coefficient of learning vector C associated with matrix D shall be based on continuous non-invasive readings.

In the example of the triangular learning matrix D, although each learning vector or row of matrix, D, was, in the above example at least, generated from a particular occasion on which non-invasive measurements were taken, and it would seem that successive rows are being afforded too much weight in the matrix, counter-intuitively it may be that the more information a processor or brain has already processed, the more time it takes to learn new information and hence the more additional data may be needed on each new subject. This theory of how the digital processor learns how to measure the bioparameter non-invasively, is also consistent with how human brains assimilate information. For example, the younger one is when one is taught a new subject, the more easily it may be to learn it and memorize large amounts of information in that subject, and less connection may needed in the neural activity. In contrast, more and more complex connections are needed as one gets older and, older taking into consideration that all brain neurons are functioning without any derogation in their blood supply. Having said this, Applicant does not intend to in any way be bound by any theory, including this theory.

Up until now, method 100 may have been in a learning mode whereby information has been provided to a device containing a non-invasive and an invasive component and that information may correlate a known glucose level (known from the invasive component) to an mathematical representation (in vector form) of an electro-optical signal representing the color distribution over time of a tissue of a body part of the patient. On each occasion that the invasive reading was taken, the reading may have been transmitted to the non-invasive component. The non-invasive component may now be ready to try to figure out what the bioparameter value would be for a non-invasive reading before being told what the invasive reading says it should be. The patient may be informed of this by a display on the device stating that no further invasive readings may be necessary or some such similar message. The following steps are generally referred to as the recognition portion of the method.

Method 100 may include a further step 150 of obtaining a coefficient of learning vector, C, by multiplying an inverse matrix $D^{-1}$ of learning matrix, D by the column vector Y. This is based on the known equation that a regular matrix, D, times a column vector C equals a column vector Y. mathematically, the coefficient vector C represents a solution to a set of equations. Step 150 may also be performed after step 160 or after step 170. Step 150 may be accomplished using first digital processor 26 of non-invasive component 20 of device 10 in conjunction with software that may be operative to program first digital processor 26 to make such calculations.

Method 100 may also include a step 160 of using a digital processor, such as first digital processor 26 of non-invasive component 20 to obtain a new vector, $V^{new}$ by (i) non-invasively measuring (for example using the non-invasive components of the same device used previously) the bioparameter of the patient by using the one or more color image sensors in a non-invasive component of the device to generate a series of color images of tissue of the body part (or of another body part) of the patient and to sense a magnitude of each of the three colors at each pixel of each color image and by converting the magnitudes into a series of electric signals, to produce a signal over time reflecting a distribution of each of the three colors in the color images over time and by having the digital processor use a mathematical function to convert the signal to a scalar number and by (ii) repeating substep "(i)" of step 160 n times to form a vector $V^{new}$, without necessarily using the same mathematical functions. If, for example the learning matrix, D is triangular and is of a dimension 9 by 9 having upper triangular zeroes as entries, the new vector, may have 9 non-zero entries forth recognition procedure. If $V^{new}$ is to be inserted into the matrix D for generating new matrix $D^{new}$ of new dimension 10 by 10, additional function shall be added to generate the $10^{th}$ entry in $V^{new}$.

When in step 160 it states "by using the one or more color image sensors in a non-invasive component of the device to generate a series of color images" it may be necessary to have the "one or more color image sensors" used in step 160 be the same identical "one or more color image sensors" used in step 120 to generate the learning vectors. If not, it may be necessary that the one or more sensors of step 160 at least have the same technical specifications as the one or more sensors of step 120 so as to produce the same result. The same applies when the variable sensors are not color image sensors but are sensors of other variables. For the same reasons, it may also be useful for the number of color image sensors or variable sensors to be the same in step 160 as in step 120.

The non-invasive component 20 of the device 10 (or the device 10 in general) may process the entries of new vector, $V^{new}$ in the following manner. Even though the following calculations were not mentioned previously for steps 100 through 150 that is only because it may be assumed that the device until now did not have enough information to successfully arrive at a bioparameter value for the patient since the learning matrix base was too small.

Method 100 may further include a step 170 of utilizing a digital processor to use the entries of $V^{new}$ to form a regular matrix, $D^{new}$, of n by n size and whose structure of non-zero elements is identical to a structure of non-zero elements of learning matrix, D. This may be accomplished in many different ways. One purely illustrative manner of accomplishing this is as follows. Suppose original learning matrix, D has a triangular structure of non-zero elements. Then a triangular structure of non-zero elements of $D^{new}$, of n by n size may be arrived at by taking the first entry of $V^{new}$ and inserting it into the first row of $D^{new}$. The second row of $D^{new}$ may be arrived at by repeating the first entry of Vnew in the first entry of this second row and then using the second entry of $V^{new}$ as the second entry of the second row of $D^{new}$. Similarly, the third row of $D^{new}$ may be comprised of the first entry of $V^{new}$, the second entry of $V^{new}$ and the third entry of $V^{new}$. Similarly, with the fourth, fifth, sixth, seventh, eighth and ninth rows of $D^{new}$ (where in this example the size of the matrix is 9 by 9).

Method 100 may further include a step 180 of using the digital processor to perform a matrix vector multiplication of $D^{new}$ by coefficient of learning vector, C, to create a column vector of non-invasive bioparameter measurement, R. Column vector R represents potentially true bioparameter values for the patient since it was arrived at by using the coefficient of learning vector, C, previously calculated between the learning matrix and the invasive readings of column vector, Y. Step 180 may also include comparing entries of R with entries of Y to find one entry of R which represents a calibrated bioparameter value for the patient. For example, one may compare entries of column vector R with entries of column vector Y to find a unique (i.e. a single) instance of an entry, i, such that an ith entry of vector R and an ith entry of vector Y are sufficiently close in magnitude using a pre-determined standard of mathematical closeness (for example 20% off). If more than one such entry exists that is close enough, then there is no single such entry. Concomitantly, if no entry of the R vector is within the pre-determined mathematical margin of error, purely by way of example 20%, of its corresponding entry in the Y vector, then in both cases the device may display a message saying "try again" (indicating that no decision can be made). If such message repeats itself for example three times, a vector $V^{new}$ may then be included in the matrix D generating a new expended calibrated matrix $D_{exp}$ and the coefficient vector C thereof. However, it should be note that the learning matrix D may be expanded even if the device was able to find a unique ith entry of R that matches the ith entry of Y within the pre-defined variance. One may simply want to expand the learning matrix to make the device better.

Accordingly, in some versions of method 100 a further step would be creating an expanded learning matrix. Initially, the expanded learning matrix, $D_{exp}$ may be of (n+1) by (n+1) size and may be created by (i) incorporating $V^{new}$ into learning matrix D and by having the digital processor use a mathematical function to convert the signal of step "(f)" to a (n+1)th scalar number and adding the (n+1)th scalar number alongside $V^{new}$ to maintain expanded learning matrix $D_{exp}$ as a regular matrix. Going back to the example where the learning matrix D was originally 9 by 9 in size, when expending the learning matrix, vector $V^{new}$ may form the tenth row of $D_{exp}$, and may have nine entries. In order to keep the matrix regular, a further non-zero entry may be generated using a mathematical function on the same signal arising from the non-invasive measurement used in $V^{new}$. In addition, zero entries may be inserted into the $10^{th}$ column of the first nine rows. In general, it should be understood that the above-described method of generating the regular matrix for the method and system of the present invention is not unique and that there are many other ways of generating this regular matrix. The present invention is broadly disclosing a process of self calibration.

This further step may also include testing the accuracy of the calibrated bioparameter value by taking a further invasive bioparameter measurement as in step 110 to expand column vector Y to (n+1) elements and transmitting this further invasive bioparameter measurement to the non-invasive component to be incorporated into vector Y so that vector Y (which may be called "$Y_{exp}$") is the same length as expanded learning matrix, $D_{exp}$. In some scenarios, the substep of taking a further invasive bioparameter measurement as in step 110 to expand column vector Y to (n+1) elements and transmitting this further invasive bioparameter measurement to the non-invasive component may happen automatically even if matrix D is not to be expanded. In other words, transmitting the further invasive bioparameter measurement may be done in a way that the measurement does not get incorporated by the non-invasive component into vector Y, but rather stores it, until a decision is made to expand the matrix D, in which case this data would only then be incorporated into vector Y.

This expansion of learning matrix $D_{exp}$ may be further continued to a size of (n+m) by (n+m) where in is greater than 1.

It may be appreciated that any of the steps of the methods of the present invention involving mathematical calculations may be implemented using software programs in conjunction with one or more digital processors that be in non-invasive component 20 or may be accessible to some part of device 10.

Once the matrix has been expanded, one may want to further test the ability of the non-invasive component to measure the bioparameter. This may be done by obtaining a new coefficient of learning vector, $C^{new}$ by multiplying an inverse matrix $D_{exp}^{-1}$ of matrix, $D_{exp}$ by the expanded column vector, $Y^{new}$, and by repeating steps 160, 170 and 180 except that in repeating these steps (160, 170, 180) we may substitute either (n+1) or whatever the current learning matrix size is for n in such steps. The result may be an improved calibrated bioparameter value for the patient.

In cases where the bioparameter is glucose, it is known that patients having diabetes go to a laboratory every three months and take an invasive glucose test called the hemoA1C test. This test, which is considered a reliable invasive glucose test, may be used as a further reference point for verifying the calibration. Accordingly, the method may also be used to test hemoA1C if the invasive references for the matrix D are hemoA1C. In case of direct glucose references, A1C may be used for verification of the calibration verification during every three months period. Accordingly, method 100 may include a further step of periodically inserting A1C results and using the A1C results converted to approximate glucose readings for the verification procedure. For example, if glucose was calibrated between 50 mg/dl to 300 mg/dl and the latest valid A1C reflects average of 400 mg/dl, additional calibration may be needed to cover the range between 300 mg/dl and 400 mg/dl.

The novel calibration procedure utilizes a matrix, D, that in any stage of evolution is regular, i.e. has an inverse. There are many ways to achieve that goal. For example, the first digital processor 26 may create the regular matrix D wherein each new vector added to the matrix, D, increases all previous rows with one additional zero in the last column wherein the new added vector now has N+1 non-zero components. In this case, matrix, D, may have a triangular shape, with zeroes in the upper triangle and non-zero components in the lower triangle. Such a matrix is regular. In other words, each row in the matrix, D, may be a list of non-invasive readings and the number of elements in the list may be the number of the row. For example, the first row of the matrix may have one entry, the second row, two entries, the third row, three entries etc. This is merely one way of ensuring that the matrix created is a regular matrix. Alternatively, the matrix may be square such as an "n by n" matrix, with entries filled in for generating independent rows and columns.

Universal Calibration

Up to now, the method of the present invention may be making use of the same subject to thereby create or refine device 10 until it is custom-tailored to the particular subject/patient. The device 10 described up to now may therefore be called a person calibration device 10. The method and apparatus of the present invention may also be used to collect data from many subjects and thereby use patients in the repeatings of step 140 of method 100 that are different from one another and different from the patient of step 110 of method 100. For example, patients may connect a device 10 to a computer and upload their bioparameter data through the Internet or a telecommunications network to generate a bioparametric value that may correspond to a cluster of individuals. Accordingly, all collected individual measurements for a bioparameter may be used to create a universal matrix, $D^{universal}$ instead of a matrix D for the individual. Just as with regular matrix D, the matrix $D^{universal}$ may also be a regular matrix.

A cluster is a group of individuals that shares certain demographic characteristics such as age, ethnicity, gender, geography, etc. Accordingly, if all collected individuals providing bioparameter readings are from a cluster, the measurements may be used to create a regular matrix that may be referred to as a cluster matrix $D^{cluster}$ for a cluster of patients.

Furthermore, the same may be done for a universe of a population by collecting data from many clusters or by collecting data independent of the shared characteristics of a cluster. In this case, step 140 of method 100 may involve patients that are different from one another and different from the patient of step 110 of method 100 in order to create a universal matrix, $D^{universal\ 1}$ of the bioparameter for an entire population. In some scenarios, them step 140 may involve obtaining the plurality of learning vectors using different patients having common characteristics and collecting data of the non-invasive and invasive measurements through a telecommunications network, thereby creating a learning matrix, $D^{cluster}$ representative of the bioparameter of a cluster of patients. In addition, a step of method 100 may include obtaining the plurality of learning vectors in step 140 using different patients having common characteristics and collecting data of the non-invasive and invasive measurements through a telecommunications network, thereby creating a learning matrix, $D^{universal}$ representative of the bioparameter of an entire population.

Accordingly, device 10 may be a universally calibrated device as opposed to a device 10 that was calibrated to a specific individual. By collecting and processing personal calibration data, a manufacturer of a device 10 may be able to provide to consumers a device 10 that has been universally calibrated. In some embodiments, a Universal-Personal calibration device 10 may be created. In this case, a universal calibration device 10 may have the ability to be further calibrated by the individual who purchases the device in accordance with the method and apparatus described for a "personal calibration device" 10. When the purchaser does so, the device 10 may be referred to as a universal-personal device 10.

The present invention may also be described as a method 200 of producing a portable bioparameter-monitoring medical device custom-tailored to a patient. In such case, method 200 may include a step 210 of providing directly or indirectly to a patient a medical device 10 as described above having (i) a non-invasive component capable of generating a non-invasive bioparametric reading of the patient's bioparameter upon insertion by the patient of a body part into the non-invasive component, the non-invasive component including a first digital processor for processing digital color images of part of the body part and representing the digital images as a signal over time, and having (ii) an invasive component for invasively measuring the bioparameter for example from blood of the patient and obtaining an invasive bioparametric reading for the patient, the invasive component also including a second digital processor for transmitting the invasive bioparametric reading to the first digital processor of the non-invasive component.

Method 200 may also have a step 220 of custom-tailoring the device to the subject by calibrating the non-invasive component to the patient. This may be accomplished by (i) invasively measuring the bioparameter of the patient using the invasive component, (ii) transmitting the invasive bioparameter readings to the non-invasive component, and (iii) non-invasively measuring the bioparameter of the patient within a proximity time of the invasive measuring an by using mathematical functions to represent the signal obtained from the non-invasive measurements as a regular matrix using the procedure described in relation to method 100. Substeps (i), (ii) and (iii) may be performed enough times that the digital processor has sufficient correlations between non-invasive bioparametric readings and invasive bioparametric readings to be able to measure the bioparameter using a non-invasive bioparameter reading at a pre-defined level of threshold acceptability.

In general, device 10, for example non-invasive component 20 (or if appropriate in some cases, invasive component 30), may be programmed to perform several functions including:

(a)(i) use a mathematical function to convert the signal to a scalar learning number and (ii) repeat step "(a)(i)", without necessarily using the same mathematical functions, to form a learning vector that corresponds to a scalar invasive bioparameter reading entry of column vector Y;

(b) form n by n learning matrix, D, that is a regular matrix, by repeating step "(a)" to non-invasive readings and invasive readings enough time that the digital processor has sufficient correlations between non-invasive bioparametric readings and invasive bioparametric readings to be able to measure the bioparameter based on a non-invasive bioparameter reading of the bioparameter at a pre-defined level of threshold acceptability;

(c) to obtain a coefficient of learning vector, C, by multiplying an inverse matrix $D^{-1}$ of matrix, D by the column vector, Y;

(d) generate a new vector, $V^{new}$ when a user non-invasively measures the bioparameter of the patient by using the one or more color image sensors in the non-invasive component of the device to generate a series of color images of tissue of the body part and by having the digital processor use a mathematical function to convert the signal to a scalar number and doing so n times to form $V^{new}$, without necessarily using the same mathematical functions;

(e) use the entries of $V^{new}$ to form a regular matrix, $D^{new}$, of n by n size and whose structure of non-zero elements is identical to learning matrix, D, and (f) use the digital processor to perform a matrix vector multiplication of $D^{new}$ by coefficient of learning vector, C, to create a vector of non-invasive bioparameter measurement, R, and comparing entries of R with entries of Y to find one entry of R which represents a calibrated bioparameter value for the patient.

In order for non-invasive component 20 to make a correlation between non-invasive bioparametric readings and invasive bioparametric readings to be able to predict at a threshold level further invasive bio-parametric readings based on non-invasive bioparametric readings, first digital processor 26 may use an industry standard to define a threshold correlation between the non-invasive readings and the invasive readings. This could for example be $R^2=0.9$ or $R^2=0.85$, where $R^2$ measures the linearity of the correlation between two variables.

Device 10, for example non-invasive component 20 (or if appropriate, invasive component 30), may also be programmed to create an expanded learning matrix $D_{exp}$ of (n+1) by (n+1) size by (i) incorporating $V^{new}$ into learning matrix D and by having the first digital processor use a mathematical function to convert the signal of "(f)" to a (n+1)th scalar number and adding the (n+1)th scalar number alongside $V^{new}$ to maintain expanded learning matrix $D_{exp}$ as a regular matrix and by incorporating further invasive bioparameter measurements to expand column vector Y (n+1) elements and transmit the further invasive bioparameter measurement to the non-invasive component. Similarly, the non-invasive component (or if appropriate, invasive component 30) may be programmed to further expand the learning matrix as described in method 100.

It should be understood that the term "digital processor" excludes human brains and includes large and small processors including microprocessors. Wherever in the method or system of the present invention "a digital processor" performs a function or task and later in the method or system it further states that "a digital processor" performs a further task or function, it should be understood that while the two digital processors do not have to be the seine digital processor, it may be preferred that they be the same digital processor because if they are different digital processors the invention may require that the two digital processors be such as to produce the same identical output. To have them produce the same output may require that the two digital processors, for example, have identical specifications. This may mean, for example having the same speed, using the same number of bits, etc. In addition, the term "optical light source" excludes the human eye. The term "patient" is not limited to those with medical conditions and simply denotes a user of the medical device. It is also noted that implantable sensors, coated wires, enzyme-covered skin piercing devices, blister formation and abrasion of the skin to cause fluid leakage are not considered non-invasive but are in the category of "minimally" invasive.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of monitoring a bioparameter, comprising:
   (a) invasively measuring the bioparameter of a patient using an invasive component of a bioparameter monitoring device, transmitting an invasive bioparameter reading to a non-invasive component of the bioparameter monitoring device and storing the invasive bioparameter reading in the non-invasive component;
   (b) within a proximity time of step "(a)", one or more variable sensors in the non-invasive component of the device generating a series of data about tissue of a body part of the patient, sensing a magnitude of a sensed variable at each variable sensor, and converting the magnitudes into a series of electric signals, the signal representing a non-invasive measurement of the bioparameter of the patient;
   (c) one or more processors of the non-invasive component programmed to convert the signal to a scalar learning number (i) using a mathematical function to convert the signal to a scalar learning number and (ii) repeating step "(c)(i)", without necessarily using the same mathematical function, to form a learning vector that corresponds to a scalar invasive bioparameter reading entry of a column vector Y;
   (d) from a plurality of learning vectors, the one or more processors forming an n by n learning matrix, D, that is a regular matrix, by repeating steps "(a)" through "(c)" enough times that the one or more processors have sufficient correlations between non-invasive bioparametric readings and invasive bioparametric readings to be able to measure the bioparameter using a non-invasive bioparameter reading at a pre-defined level of acceptability;
   (e) the one or more digital processors obtaining a new vector, $V^{new}$ by (i) non-invasively measuring the bioparameter of the patient by using the one or more variable sensors in the non-invasive component of the device to generate a series of data about tissue of a body part of the patient, and to sense a magnitude of a sensed variable at each variable sensor and by converting the magnitudes into a series of electric signals over time and by having the one or more digital processors use a mathematical function to convert the signal to a scalar number and by (ii) repeating step "(e)(i) n times to form $V^{new}$, without necessarily using the same mathematical functions; and either
   (I)(a) using the entries of $V^{new}$ to form a regular matrix, $D^{new}$, of n by n size and whose structure of non-zero elements is identical to a structure of non-zero elements of learning matrix, D; and
   (I)(b) using the one or more digital processors to obtain a coefficient of learning vector, C, by multiplying an inverse matrix $D^{-1}$ of learning matrix, D by the column vector Y and to perform a matrix vector multiplication of $D^{new}$ by coefficient of learning vector, C, to create a column vector of non-invasive bioparameter measurement, R, and comparing entries of R with entries of Y to find one entry of R which represents a calibrated bioparameter value for the patient; or
   (II) using the one or more digital processors to compare entries of $V^{new}$ with rows of learning matrix, D to find a best match involving an ith row of learning matrix, D and using the ith entry of Y as a calibrated bioparameter value for the patient.

2. The method of claim 1, further comprising creating an expanded learning matrix $D_{exp}$ of (n+1) by (n+1) size by (i) incorporating $V^{new}$ into learning matrix D and by having one or more digital processors use a mathematical function to convert the signal of step "(e)" to a (n+1)th scalar number and adding the (n+1)th scalar number alongside $V^{new}$ to maintain expanded learning matrix $D_{exp}$ as a regular matrix and by (ii) testing an accuracy of the calibrated bioparameter value by taking a further invasive bioparameter measurement as in step "(a)" to expand column vector Y to (n+1) elements and transmitting the further invasive bioparameter measurement to the non-invasive component.

3. The method of claim 2, further comprising continuing to expand learning matrix $D_{exp}$ to a size of (n+m) by (n+m) where m is greater than 1.

4. The method of claim 2, further comprising further testing an ability of the non-invasive component to measure the bioparameter by obtaining a new coefficient of learning vector, $C^{new}$ by multiplying an inverse matrix $D_{exp}^{-1}$ of matrix, $D_{exp}$ by the expanded column vector, Y, and by repeating steps "(e)", "(I)(a)" and "(I)(b)" except substituting (n+1) for n in steps "(e)", "(I)(a)" and "(I)(b)" to obtain an improved calibrated bioparameter value for the patient.

5. The method of claim 1, wherein the structure of the non-zero entries of learning matrix, D, is triangular such that a magnitude of entries in each succeeding row increases by an integer.

6. The method of claim 5, wherein the integer is one and wherein a first row of learning matrix, D, has one non-zero entry.

7. The method of claim 1, further comprising comparing entries of column vector R with entries of column vector Y to find a unique instance of an entry, i, such that an ith entry of R and an ith entry of Y are sufficiently close in magnitude using a pre-determined standard of mathematical closeness.

8. The method of claim 1, further comprising the medical device, after step "(d)", displaying a message to a user of the medical device to the effect that further invasive measurements are not needed.

9. The method of claim 1, wherein the bioparameter is glucose and wherein the method further includes periodically taking non-invasive measurements in proximity to A1C results and using the A1C results as invasive measurements transmitted to the invasive component to expand the learning matrix D and calibrate the non-invasive component in a range between a last valid A1C result and a maximum or minimum calibrated bioparameter value previously obtained.

10. The method of claim 1, wherein the mathematical function generates a scalar value representative of the signal.

11. The method of claim 1, further comprising obtaining the plurality of learning vectors in step "(d)" using different patients having common characteristics and collecting data of the non-invasive and invasive measurements through a telecommunications network, thereby creating a learning matrix, $D^{cluster}$ representative of the bioparameter of a cluster of patients.

12. The method of claim 1, further comprising obtaining the plurality of learning vectors in step "(d)" using different patients having common characteristics and collecting data of the non-invasive and invasive measurements through a telecommunications network, thereby creating a learning matrix, $D^{universal}$ representative of the bioparameter of an entire population.

13. The method of claim 1, wherein the variable sensed by the variable sensor is selected from the group consisting of temperature, conductivity and smell.

14. A portable bioparameter-monitoring medical device usable by a patient for monitoring a bioparameter of the patient, comprising:
a non-invasive component structured to receive a body part of a patient and configured to generate non-invasive bioparametric readings of tissue of the body part upon insertion of the body part of the patient into the non-invasive component, the non-invasive component including at least one variable sensor configured to sense a magnitude of a sensed variable and generate a series of data about the tissue, the non-invasive component also including a first digital processor configured for processing the series of data into a signal over time, the signal representing a non-invasive measurement of the bioparameter of the patient;
an invasive component for obtaining an invasive bioparametric reading from blood of the patient, the invasive component also for directing automatic transmission of the invasive bioparametric reading to the first digital processor of the non-invasive component, the invasive bioparametric readings forming entries in a column vector, Y,
the first digital processor of the non-invasive component programmed to
(a)(i) use a mathematical function to convert the signal to a scalar learning number and (ii) repeat step "(a)(i)", without necessarily using the same mathematical functions, to form a learning vector that corresponds to a scalar invasive bioparameter reading entry of column vector Y;
(b) form an n by n learning matrix, D, that is a regular matrix, by repeating step "(a)" to non-invasive readings and invasive readings enough times that the first digital processor has sufficient correlations between non-invasive bioparametric readings and invasive bioparametric readings to be able to measure the bioparameter based on a non-invasive bioparameter reading of the bioparameter at a pre-defined level of threshold acceptability;
(d) generate a new vector, $V^{new}$ by using a mathematical function to convert a new signal to a scalar number and do so n times to form $V^{new}$, without necessarily using the same mathematical functions, when a user uses the at least one variable sensor in the non-invasive component to generate the new signal from a new series of data from the tissue of the body part, the new signal representing a new non-invasive measurement of the bioparameter of the patient; and
either both
(I)(a) use the entries of $V^{new}$ to form a regular matrix, $D^{new}$, of n by n size and whose structure of non-zero elements is identical to learning matrix, D, and
(I)(b) obtain a coefficient of learning vector, C, by multiplying an inverse matrix $D^{-1}$ of matrix, D by the column vector, Y and perform a matrix vector multiplication of $D^{new}$ by coefficient of learning vector, C, to create a vector of non-invasive bioparameter measurement, R, and compare entries of R with entries of Y to find one entry of R which represents a calibrated bioparameter value for the patient; or
(II) use the one, or more digital processors to compare entries of $V^{new}$ with rows of learning matrix, D to find a best match involving an ith row of learning matrix, D and using the ith entry of Y as a calibrated bioparameter value for the patient.

15. The medical device of claim 14, wherein the at least one variable sensor configured to generate a magnitude of a sensed variable at variable sensors is a color image sensor configured to generate a series of color images of the tissue of the body part and to sense a magnitude of each of three colors at pixels of each color image and wherein the first digital processor is configured for processing the series of color images into the signal over time reflecting a distribution of the three colors over time.

16. The medical device of claim 15, wherein the non-invasive component includes a light transmitting element that transmits light through a finger and generates digital color images from light exiting the finger.

17. The medical device of claim 15, wherein the discrete digital signal incorporates a red matrix representing magnitudes of red light at pixels of a digital image of the finger, a green matrix representing magnitudes of green light at the pixels and a blue matrix representing magnitudes of blue light at the pixels.

18. The medical device of claim 14, further inducing a coupling element for maintaining the invasive component operatively engaged to the non-invasive component and allowing transmission of invasive bioparametric readings from the invasive component to the non-invasive component, wherein the coupling element also permits de-coupling of the invasive and non-invasive components from one another.

19. A method of producing a portable bioparameter-monitoring medical device custom-tailored to a patient, the method comprising:
(a) providing directly or indirectly to a patient a medical device having (i) a non-invasive component capable of generating a non-invasive bioparametric reading of the patient's bioparameter upon insertion by the patient of, a body part into the non-invasive component, the non-invasive component including a first digital processor configured for processing a series of sensed variables describing the body part and representing the series of data as a discrete signal over time, and having (ii) an invasive component for measuring the bioparameter from blood of the patient and obtaining an invasive bioparametric reading for the patient, the invasive component also including a second digital processor for transmitting the invasive bioparametric reading to the first digital processor of the non-invasive component, and (iii) a coupling element for maintaining the invasive component operatively engaged to the non-invasive component and allowing transmission of invasive bioparametric readings from the invasive component to the non-invasive component, the first digital processor also for calibrating the non-invasive component so that the non-invasive bioparametric readings for the patient approximate the invasive bioparametric readings for the patient for a given bioparameter under a predefined standard of approximation; and (b) calibrating the non-invasive component to the patient by (i) invasively measuring the bioparameter of the patient using the invasive component, (ii) transmitting the invasive bioparameter readings to the non-invasive component, and (iii) non-invasively measuring the bioparameter of the patient within a proximity time of the invasive measuring using mathematical functions, and performing substeps (i), (ii) and (iii) enough times that the first digital processor has sufficient correlations between non-invasive bioparametric readings and invasive bioparametric readings to be able to measure the bioparameter using a non-invasive bioparameter reading at a pre-defined level of acceptability.

20. A non-transitory computer-readable medium having stored thereon bioparameter monitoring software, the bioparameter monitoring software executed by one or more digital processors, the execution of the bioparameter monitoring software by the one or more digital processors performing:

(a)(i) using a mathematical function to convert a signal generated by a non-invasive component reflecting a non-invasive bioparameter reading, to a scalar learning number and (ii) repeating step "(a)(i)", without necessarily using the same mathematical function, to form a learning vector that corresponds to a scalar invasive bioparameter reading entry in a column vector Y, wherein entries in column vector Y represent invasive bioparameter readings of a patient;

(b) from a plurality of learning vectors, forming an n by n learning matrix, D, that is a regular matrix, by repeating step "(a)" a pre-defined number of times, each time from newly generated non-invasive bioparameter readings and a newly generated scalar invasive bioparameter reading that is an entry for column vector, Y;

(c)(i) obtaining a new vector, $V^{new}$ by using a mathematical function to convert a further new signal to a scalar number and by (ii) repeating step "(c)(i)" n times to form $V^{new}$, without necessarily using the same mathematical functions; and (d) compare entries of $V^{new}$ with rows of learning matrix, D to find a best match involving an ith row of learning matrix, D and using the ith entry of Y as an approximated calibrated bioparameter value for the patient under a predefined standard of approximation.

21. The bioparameter monitoring software of claim 20, wherein the execution of the bioparameter monitoring software by the one or more digital processors also performs:
receiving an invasive bioparameter reading from the invasive component and storing the invasive bioparameter reading as an entry in the column vector, Y;
within a proximity time of the receiving of the invasive bioparameter reading, receiving the signal of step "(a)" from one or more variable sensors in the non-invasive component, the signal reflecting a series of data describing tissue of a body part of a patient over time; and
obtaining the new vector, $V^{new}$ in step "(c)" by receiving the further new signal from the one or more variable sensors in the non-invasive component, the further new signal reflecting data describing the tissue over time, wherein the pre-defined number of times is enough times that the one or more digital processors have sufficient correlations between non-invasive bioparametric readings and invasive bioparametric readings to be able to measure the bioparameter using a non-invasive bioparameter reading at a pre-defined level of threshold acceptability.

22. The bioparameter monitoring software of claim 20, wherein the execution of the bioparameter monitoring software by the one or more digital processors further performs: creating an expanded learning matrix $D_{exp}$ of (n+1) by (n+1) size by (i) incorporating $V^{new}$ into learning matrix D, by using a mathematical function to convert the further new signal of step "(d)" to a (n+1)th scalar number and adding the (n+1)th scalar number alongside $V^{new}$ to maintain expanded learning matrix $D_{exp}$ as a regular matrix and by receiving a further invasive bioparameter measurement to expand column vector Y to (n+1) elements.

23. The bioparameter monitoring software of claim 22, wherein the execution of the bioparameter monitoring software by the one or more digital processors further performs: continuing to expand learning matrix $D_{exp}$ to a size of (n+m) by (n+m) where in is greater than 1.

24. The bioparameter monitoring software of claim 20, wherein the execution of the bioparameter monitoring software by the one or more digital processors further performs: having the medical device, after step "(b)", directing a display to display a message to a user of the medical device to the effect that further invasive measurements are not needed.

25. The bioparameter monitoring software of claim 20, wherein the execution of the bioparameter monitoring software by the one or more digital processors further performs: expanding the learning matrix D and calibrating the non-invasive component in a range between a last valid A1C result received and a maximum or minimum calibrated bioparameter value previously received, wherein the bioparameter is glucose and wherein the learning matrix D is expanded by periodically receiving non-invasive measurements in proximity to A1C results and using the A1C results as invasive measurements for entry in the column vector, Y.

26. The bioparameter monitoring software of claim 20, wherein the execution of the bioparameter monitoring software by the one or more digital processors further performs: using the mathematical function to generate a scalar value representative of the signal.

27. The bioparameter monitoring software of claim 20, wherein the execution of the bioparameter monitoring software by the one or more digital processors further performs: creating a learning matrix, $D^{cluster}$ representative of the bioparameter of a cluster of patients, wherein the plurality of learning vectors in step "(b)" is from different patients having common characteristics.

28. The bioparameter monitoring software of claim 20, wherein the execution of the bioparameter monitoring software by the one or more digital processors further performs: creating a learning matrix, $D^{universal}$ representative of the bioparameter of an entire population of patients, wherein the plurality of learning vectors in step "(b)" is from different patients having common characteristics.

29. A method of monitoring a bioparameter, comprising:
(a) invasively measuring the bioparameter of a patient using an invasive component of a bioparameter monitoring device, transmitting an invasive bioparameter reading to a non-invasive component of the bioparameter monitoring device; and storing the invasive bioparameter reading in the non-invasive component;
(b) within a proximity time of step "(a)", one or more variable sensors in the non-invasive component of the device generating a series of data or color images of tissue of a body part of the patient, wherein the images represent interference by the tissue with emitted light, sensing a magnitude of the emitted light at each sensor, or sensing a magnitude of light in each of three colors at pixels of each color image, and converting the magnitudes into a series, of electric signals, the signal representing a non-invasive measurement of the bioparameter of the patient;
(c) one or more processors of the non-invasive component programmed to convert the signal to a scalar learning number (i) using a mathematical function to convert the signal to a scalar learning number and (ii) repeating step "(c)(i)", without necessarily using the same mathematical function, to form a learning vector that corresponds to a scalar invasive bioparameter reading entry of a column vector Y;
(d) from a plurality of learning vectors, the one or more processors forming an n by n learning, matrix, D, that is a regular matrix, by repeating steps "(a)" through "(c)" enough times that the one or more processors have sufficient correlations between non-invasive bioparametric readings and invasive bioparametric readings to be able to measure the bioparameter using a non-invasive bioparameter reading, at a pre-defined level of acceptability;
(e) the one more digital processors obtaining a new vector, $V^{new}$ by (i) non-invasively measuring the bioparameter of the patient by using the one or more variable sensors in the non-invasive component of the device to generate a series of data or color images of tissue of a body part of the patient, wherein the images represent interference by the tissue with emitted light and to sense a magnitude of emitted light at each sensor or to sense a magnitude of light in each of the three colors at pixels of each image and by converting the magnitudes into a series of electric signals over time reflecting a spatial temporal pixel color distribution and by having the one or more digital processors use a mathematical function to convert the signal to a scalar number and by (ii) repeating step "(e)(i) n times to form $V^{new}$, without necessarily using the same mathematical functions; and either
(I)(a) using the entries of $V^{new}$ to form a regular matrix, $D^{new}$, of n by n size and whose structure of non-zero elements is identical to a structure of non-zero elements of learning matrix, D; and
(I)(b) using the one or more digital processors to obtain a coefficient of learning vector, C, by multiplying an inverse matrix $D^{-1}$ of learning matrix, D by the column vector Y and to perform a matrix vector multiplication of $D^{new}$ by coefficient of learning vector, C, to create a column vector of non-invasive bioparameter measurement, R, and comparing entries of R with entries of Y to find one entry of R which represents a calibrated bioparameter value for the patient; or
(II) using the one or more digital processors to compare entries of $V^{new}$ with rows of learning matrix, D to find a best match involving an ith row of learning matrix, D and using the ith entry of Y as a calibrated bioparameter value for the patient.

30. A non-transitory computer-readable medium having stored thereon bioparameter monitoring software, the bioparameter monitoring software executed by one or more digital processors, the execution of the bioparameter monitoring software by the one or more digital processors performing:
(a) (i) using a mathematical function to convert a signal generated by a non-invasive component reflecting a non-invasive bioparameter reading, to a scalar learning number and (ii) repeating step "(a)(i)", without necessarily using the same mathematical function, to form a learning vector that corresponds to a scalar invasive bioparameter reading entry in a column vector Y, wherein entries in column vector Y represent invasive bioparameter readings of a patient;
(b) from a plurality of learning vectors, forming an n by n learning matrix, D, that is a regular matrix, by repeating step "(a)" a pre-defined number of times, each time from newly generated non-invasive bioparameter readings and a newly generated scalar invasive bioparameter reading that is an entry for column vector, Y;
(c)(i) obtaining a new vector, $V^{new}$ by using a mathematical function to convert a further new signal to a scalar number and by (ii) repeating step "(c)(i)" n times to form $V^{new}$, without necessarily using the same mathematical functions; and
(d)(I) using the entries of $V^{new}$ to form a regular matrix, $D^{new}$, of n by n size and whose structure of non-zero elements is identical to a structure of non-zero elements of learning matrix, D; and
(II) obtaining a coefficient of learning vector, C, by multiplying an inverse matrix $D^{-1}$ of learning matrix, D by the column vector Y and performing a matrix vector multiplication of $D^{new}$ by coefficient of learning vector, C, to create a column vector of non-invasive bioparameter measurement, R, and comparing entries of R with entries of Y to find one entry of R which represents a calibrated bioparameter value for the patient.

* * * * *